(12) United States Patent
Machan et al.

(10) Patent No.: US 7,983,391 B2
(45) Date of Patent: Jul. 19, 2011

(54) SYSTEM FOR REDUCTION OF EXPOSURE TO X-RAY RADIATION

(76) Inventors: Lindsay S. Machan, Vancouver (CA); Daniel Gelbart, Vancouver (CA)

( * ) Notice: Subject to any disclaimer, the term of this patent is extended or adjusted under 35 U.S.C. 154(b) by 99 days.

(21) Appl. No.: 12/386,895

(22) Filed: Apr. 27, 2009

(65) Prior Publication Data
US 2010/0272238 A1    Oct. 28, 2010

(51) Int. Cl.
*H05G 1/64* (2006.01)
*G21K 1/04* (2006.01)

(52) U.S. Cl. ........ 378/98.2; 378/151; 378/152; 378/153

(58) Field of Classification Search .............. 378/4, 19, 378/145, 147–153
See application file for complete search history.

(56) References Cited

U.S. PATENT DOCUMENTS

| 3,649,835 | A | * | 3/1972 | Brackenbrough et al. |
| 4,143,273 | A | * | 3/1979 | Richey et al. |
| 4,489,426 | A | * | 12/1984 | Grass et al. |
| 4,766,603 | A | * | 8/1988 | Okabe et al. |
| 4,868,843 | A | * | 9/1989 | Nunan |
| 5,278,887 | A | | 1/1994 | Chiu et al. |
| 5,422,926 | A | * | 6/1995 | Smith et al. |
| 5,568,533 | A | * | 10/1996 | Kumazaki et al. ............ 378/156 |
| 5,621,779 | A | * | 4/1997 | Hughes et al. ................. 378/65 |
| 6,792,078 | B2 | * | 9/2004 | Kato et al. ..................... 378/152 |
| 2006/0067481 | A1 | * | 3/2006 | Morton ......................... 378/151 |

FOREIGN PATENT DOCUMENTS
JP        2005095345    *  4/2005
* cited by examiner

*Primary Examiner* — Irakli Kiknadze
(74) *Attorney, Agent, or Firm* — Oyen Wiggs Green & Mutala LLP

(57) ABSTRACT

To reduce X-ray exposure, an area of interest is selected in the image. The image of the selected area is updated frequently, comparable to rate of updates used today for the whole image. The rest of the image is updated at a significantly lower rate. Since the area of interest normally is a small part of the overall area, the total exposure is reduced significantly. A movable X-ray shield placed near the X-ray source blocks the radiation from areas outside the area of interest. The shield automatically retracts when the complete image is updated. The area of interest can be selected by the user or automatically selected based on activity in the image.

16 Claims, 3 Drawing Sheets

SYSTEM FOR REDUCTION OF EXPOSURE TO X-RAY RADIATION

FIELD OF THE INVENTION

The invention is in the medical field and in particular in real-time X-ray or fluoroscopy.

BACKGROUND OF THE INVENTION

The use of real-time, or continuous, X-ray is increasing rapidly because of the increased use of percutaneous medical procedures such as coronary stents, atrial ablation and gastric procedures. The doctors or other users in the operating room are forced to wear heavy lead aprons and sometimes goggles made of thick lead glass to avoid the cumulative effects of the X-ray radiation. A smaller dose of X-ray may reach persons far away from the X-ray machine. The most common X-ray procedure is fluoroscopy, in which a portable arm carries an X-ray source at one end and a digital X-ray image sensor at the other end, with the patient placed between them. A screen connected to the image sensor via an image processing system displays real time images of the procedure. Some previous attempts to reduce the radiation used stationary lead shields, adjusted by the user. This is a time consuming operation. Other prior art solutions use an electrically controlled masks that allows radiation to reach only part of the image. This is less than optimal, as without seeing the whole image it is difficult for the doctor to orient himself. The invention takes advantage of the fact that most of the image is changing very slowly and does not need as frequent updates as the area of interest. It is an object of the invention to reduce the X-ray exposure both for the patient and the doctor without degrading the image quality. A further object is to supply a system than can easily be incorporated into the design of existing fluoroscopy systems, or used as an add-on to existing systems. A further object is to introduce minimal changes in the use of the X-ray equipment compared to current practice, in order to avoid re-training. These and further objects will become clear by reading the disclosure in conjunction with the drawings.

SUMMARY OF THE INVENTION

To reduce X-ray exposure, an area of interest is selected in the image. The image of the selected area is updated frequently, comparable to rate of updates used today for the whole image. The rest of the image is updated at a significantly lower rate. Since the area of interest normally is a small part of the overall area, the total exposure is reduced significantly. A movable X-ray shield placed near the X-ray source blocks the radiation from areas outside the area of interest. The shield automatically retracts when the complete image is updated. The area of interest can be selected by the user or automatically selected based on activity in the image.

DETAILED DISCLOSURE

Figure 1:
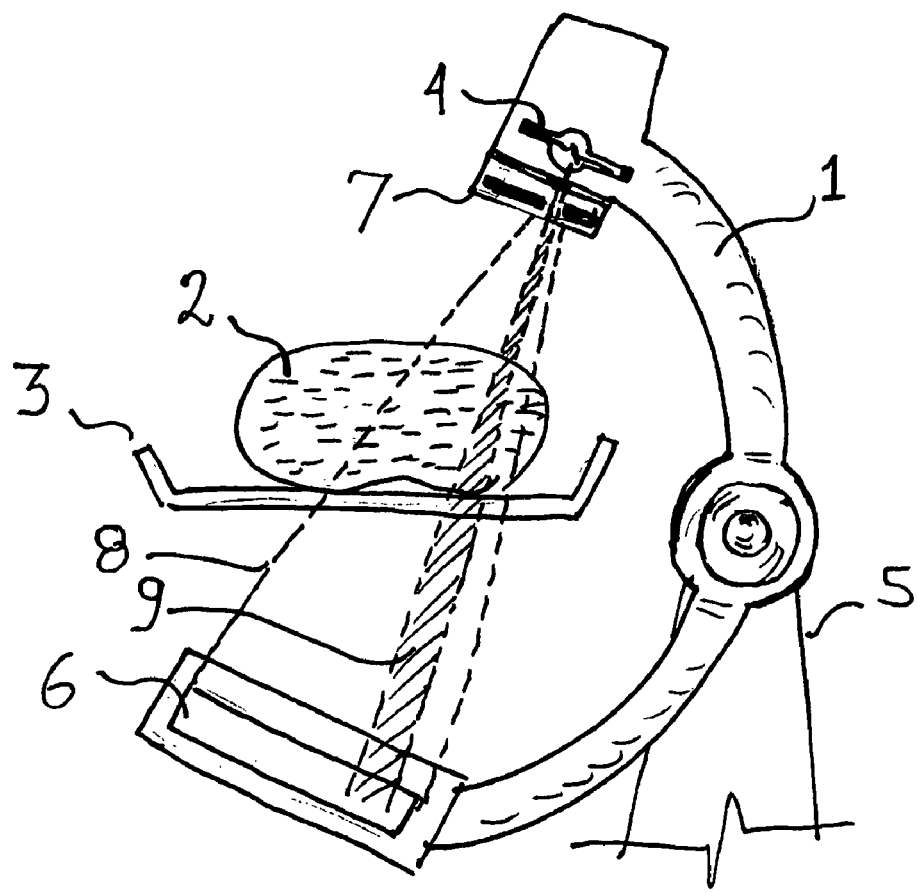
FIG. 1 shows a simplified view of a fluoroscopy system.

A typical X-ray fluoroscopy system is shown in FIG. 1. An arm 1 carries an X-ray source 4 at one end and a digital X-ray image sensor 6 at the other end. A patient 3 is supported on table 3 and placed between source 4 and sensor 6. The system is typically mounted on a cart (not shown) via column 5 which allows positioning arm 1 in any position relative to patient 2. An automatic X-ray masking unit 7 is added near source 4. Masking unit 7 can automatically change the beam from a wide beam 8 to a narrow beam 9 directed at the area of interest. Since the radiation is mainly used in the form of narrow beam 9 and only used in the full width beam 8 to update the less important image parts, a significant reduction of radiation is achieved both for the patient and the doctor. In this disclosure the terms X-ray and fluoroscopy are used interchangeably and the terms "mask" and "shield" should be broadly interpreted as anything that can interfere with the normal propagation of X-ray, not only by absorption but also by refraction, diffraction or any other interaction mechanism.

Figure 2:
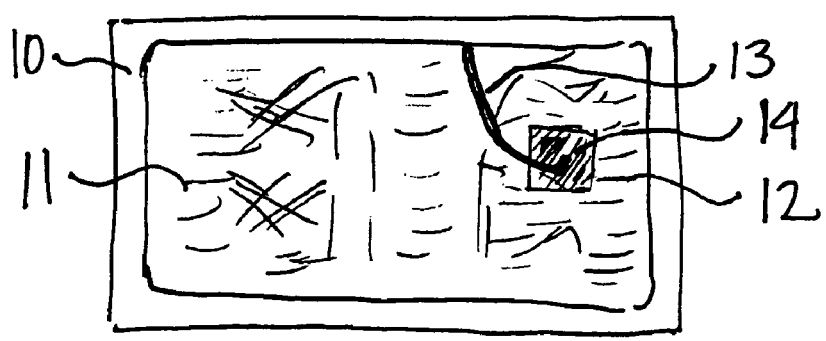
FIG. 2 shows the appearance of a fluoroscopy display according to the invention.

The reduction of radiation can be appreciated from FIG. 2. A screen 10 displays a real-time X-ray image 11. By the way of example, a tool such as guide-wire 13 is inserted into the body. The area of interest is at the tip 14 of the guide wire, since the rest of the wire is not free to move (e.g. it is usually confined to a blood vessel or other lumen). A small area of interest 12 is chosen and this area is updated at the full rate. The rest of the image 11 is updated at a significantly lower rate. By the way of example, if the area of interest is 10% in width and 10% in height of image 11 it occupies 1% of the area. If this 1% is updated at the full rate while the rest of the image is updated at $\frac{1}{30}$ of the rate (i.e. once per second compared to 30 frames per second), the total radiation will be 1%+$\frac{1}{30}$ of 100%=4.3% of the previously used dose. This represents a reduction of 23 fold. In practical terms this will allow the lead aprons to be significantly lighter and may eliminate the need for the lead glass goggles. The area of interest 14 can be manually selected by the user or can be automatically selected by a computer based on the activity in the image 11. Typically areas with very slow changes in image 11 are of little interest. Areas of interest, like the end of a guide wire or an angioplasty balloon, change rapidly as they are being manipulated by the doctor. By looking at the rate of change in the image the area of interest can be automatically selected. Sometimes there could be multiple areas of interest, requiring multiple windows 14 in image. The higher radiation level area 14 is exposed to radiation comparable to the radiation density the whole area was exposed to in prior art systems. The areas outside the higher radiation area 14 are now exposed to a significantly lower radiation level.

Figure 4:
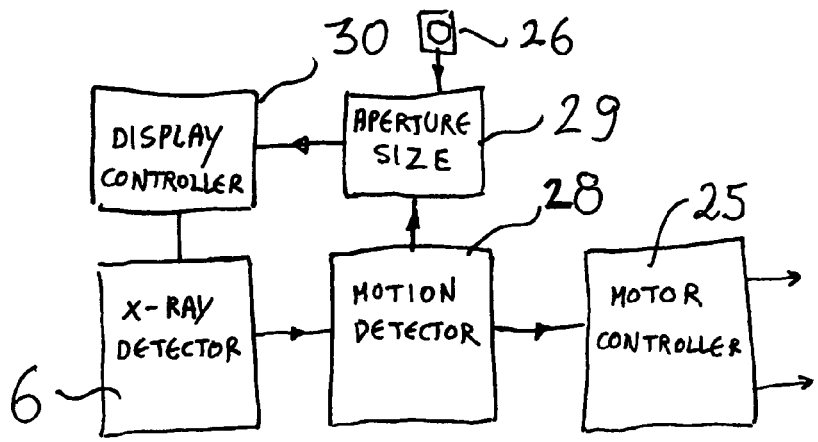
FIG. 4 is a block diagram of an automatic aperture selector.

A block diagram of such automatic selection based on activity is shown in FIG. 4. An X ray image sensor, or detector, 6 is connected to a display via a computer or display controller 30. A motion detector 28 determines the area of interest by monitoring the rate of change in the image. The algorithms for rate of change are well known in the art, and are typically based on subtracting consecutive frames. The larger the rate of change, the larger the difference between consecutive frames. An aperture size is selected by module 29, covering the area or areas where the rate of change exceeded a set threshold. This is fed to display controller 30 as well as to the controller 25 activating the variable masking mechanism which is explained later. A manual over-ride aperture control 26 can also be used to allow the user to change the dimensions of the selected aperture.

The variable aperture mask comprises of X-ray shields mounted on actuators. X-ray shields are typically made of lead but any heavy metal and some non-metals can be used. When lead is used the thickness of the shield, or mask, is in the range of 1-20 mm.

The actuators control the shields to form an aperture. This aperture limits the radiation for most of the time. The actuators open up the aperture to expose the whole image for a small fraction of the time, typically between 1% to 10% of the time.

Figure 3:
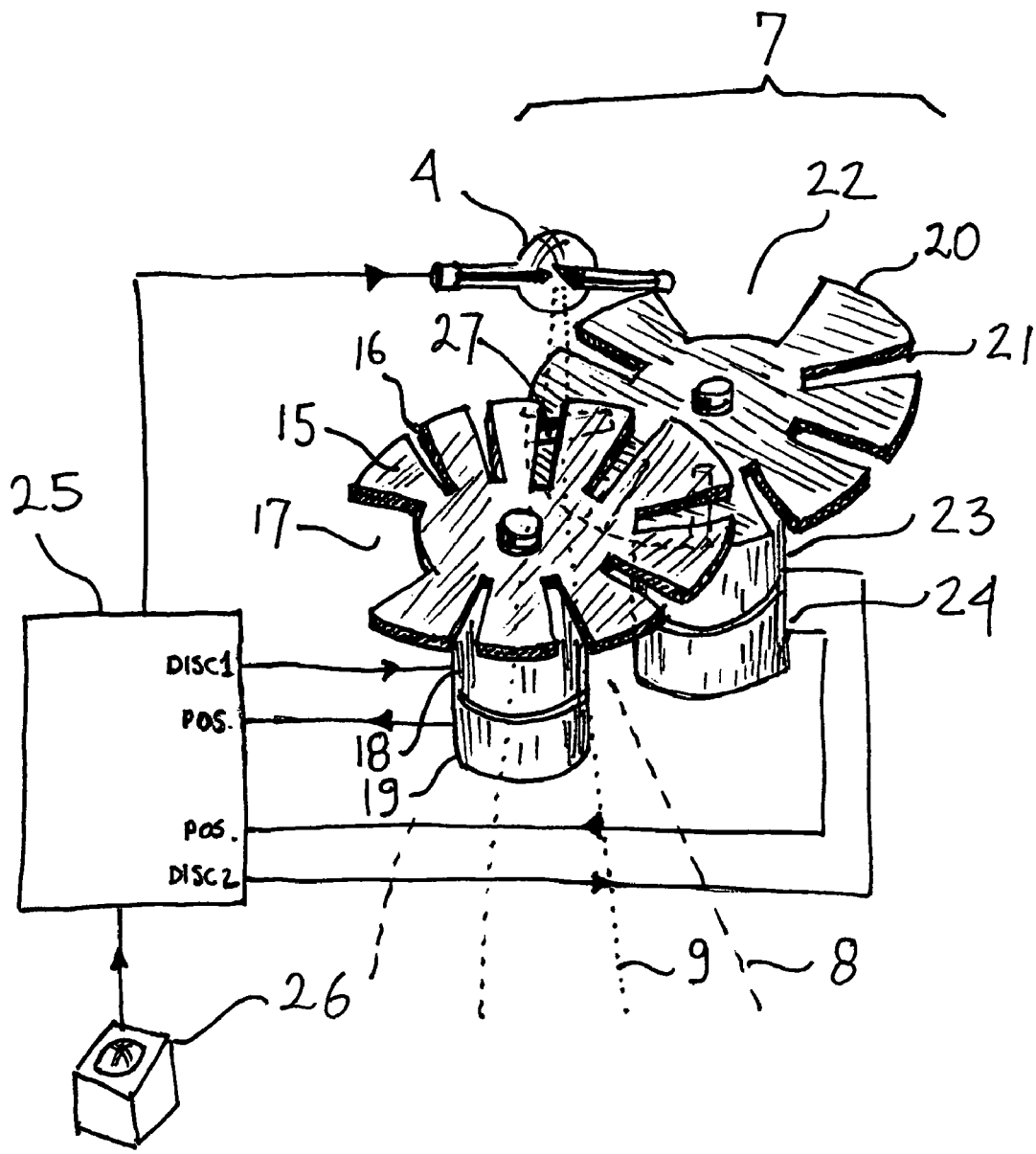
FIG. 3 is an isometric view of a rotary automatic masking unit.
Figure 5:
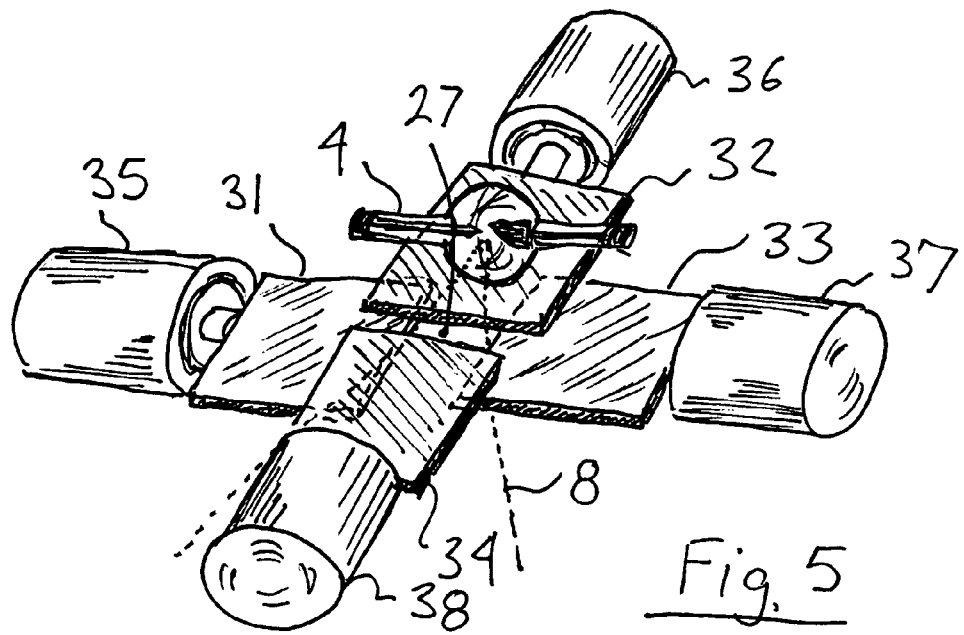
FIG. 5 is an isometric view of a linear automatic masking unit.

Two embodiments are disclosed, one based on rotary actuators is shown in FIG. 3 and one based on linear actuators is shown in FIG. 5.

Referring now to FIG. 3, a masking unit 7 comprises of two rotary masks 15 and 20, typically made of lead sheet, rotated by two servo motors 18 and 23, having shaft encoders 19 and 24. A motor controller 25 controls the speed and relative position of the motors and triggers the activation of the X-ray source 4 whenever the masks are at the correct position. Each mask has a plurality of narrow slots 16 and 21 as well as at least one wide slot 17 and 22. When the wide slots 17 and 22 overlap the full image is exposed by a wide beam 8. When the narrow slots overlap a small aperture 27 is formed, allowing only a narrow beam 9 to expose the patient and update the area of interest in the image. The relative position of aperture 27 in the image is controlled by advancing or retarding the position of one motor relative to the other. For example, if the position of mask 15 will be advanced clockwise relative to mask 20, aperture 27 will move to the right. Similarly, if the position of mask 20 will be advanced clockwise, aperture 27 will move up. Masks 15 and 20 can be continuously rotated or stepped by stepper motors. The can be slaved to the firing rate of X-ray source 4 or the firing of source 4 can be slaved to the position of the masks. For highest speed operation (i.e. the highest rate of frames per second) it is best to have the masks rotate continuously and slave the firing of the source to the position of the masks. The system of FIG. 3 allows positioning of the aperture 27 anywhere in the image but does not allow changing the aperture size. By replacing each mask wheel by two parallel wheels, each having its own motor, the size of the mask can be controlled by the relative position of the mask wheels, as the mask will be the overlap of the two slots in each direction. An alternate embodiment has only two wheels, as shown in FIG. 3, but each wheel has multiple sets of slots, each set of a different width. This allows selecting the aperture width and aperture height independently is discrete steps. The desire aperture position and size can be selected automatically or manually, by using an interface device such a trackball 26 or any other pointing device such as a computer mouse, joystick, touch screen etc.

A linear masking embodiment is shown in FIG. 5. Masking shields 31, 32, 33 and 34 are moved by linear actuators 35, 36, 37 and 38. The opening between the masks forms the aperture 27. The operation is similar to the rotary mask. Both the position and size of aperture 27 is easily variable. Most of the time aperture 27 is small, periodically opening for a full exposure. Actuators 35-38 can be of the moving coil type, commercially available from companies such as Kimco (www.beikimco.com/actuators_linear.php).

They can incorporate linear encoders (not shown) when operated in close-loop mode. The linear masking is typically more versatile than the rotary but slower (for a given size and input power).

Both types of masking units can be easily added to existing X-ray equipment by mounting them just below the X-ray source. Other methods of changing the X-ray beam dimensions can also be used, such as multi-electrode X-ray tubes. Such methods should also be considered part of the invention. Another embodiment can take advantage of longer integration times for the slower changing image areas. In this embodiment the X-ray shields are made of an X-ray attenuating material, such as thin lead. The transmission of the attenuator can be in the range of 1% to 30%. The shields are positioned once to form a given aperture and only moved if aperture needs to change. The area in the aperture receives full X-ray exposure, while the rest of the image receives attenuated exposure. Since the rest of the image is updated slowly, longer integration times leading to higher sensitivity can be used.

The invention claimed is:

1. An X-ray imaging system for displaying an image on a monitor comprising means for selecting an area of interest in said image and exposing said area of interest to a higher radiation level than the rest of the image, wherein said higher radiation is a result of a higher image updating rate, and wherein the area of interest is automatically selected by the system.

2. A system as in claim 1 comprising an automatically variable mask capable of limiting the radiation pattern in two dimensions and wherein said mask is operable to repeatedly switch between two or more positions during imaging.

3. A system as in claim 2 wherein said variable mask is formed by overlapping at least two X-ray shields mounted on rotary actuators.

4. A system as in claim 2 wherein said variable mask is formed by overlapping at least two X-ray shields mounted on linear actuators.

5. A system as in claim 2 wherein said mask widens periodically to stop limiting the radiation pattern.

6. A system as in claim 2 wherein firing of an X-ray source is synchronized to the position of the variable mask.

7. A system as in claim 1 wherein said higher radiation level is created by a variable aperture in an X-Ray blocking mask.

8. A system as in claim 1 wherein said higher radiation level is created by a variable aperture in an X-Ray attenuating mask.

9. A system as in claim 1 wherein said higher radiation level is created by a variable aperture in an X-Ray blocking mask, said mask created by overlapping at least two X-ray shields.

10. A system as in claim 1 wherein the area of interest is automatically selected by the system based on rates of changes in the image.

11. A system as in claim 1 wherein both the location and shape of the area of interest are automatically selected.

12. An X-ray imaging system for displaying an image on a monitor wherein part of said image is created at a higher radiation level than the rest of the image, wherein said higher radiation is a result of a higher image updating rate, and wherein an area of interest is automatically selected by the system.

13. A system as in claim 12 wherein the area of interest is automatically selected by the system based on rates of changes in the image.

14. A method for X-ray imaging comprising the following steps:
selecting an area of interest in an image by using a variable X-ray mask and updating the image of the area of interest at full rate;
updating the rest of the image at a lower rate by periodically opening up said mask during imaging; and
displaying the image that is a combination of the area of interest and the rest of the image.

15. A method as in claim 14 wherein selecting the area of interest comprises manually selecting the area of interest.

16. A method as in claim 14 wherein selecting the area of interest comprises automatically selecting the area of interest.

* * * * *